US010660528B2

(12) United States Patent
Bailey et al.

(10) Patent No.: US 10,660,528 B2
(45) Date of Patent: May 26, 2020

(54) METHOD OF USING AN IN VIVO SENSOR HAVING DIFFERENTIAL MATERIAL PROPERTIES

(71) Applicant: Vactronix Scientific, LLC, Fremont, CA (US)

(72) Inventors: Steven R. Bailey, San Antonio, TX (US); Christopher T. Boyle, Flushing, NY (US); Denes Marton, San Antonio, TX (US); Christopher E. Banas, Breckenridge, CO (US)

(73) Assignee: Vactronix Scientific, LLC, Fremont, CA (US)

( * ) Notice: Subject to any disclaimer, the term of this patent is extended or adjusted under 35 U.S.C. 154(b) by 0 days.

(21) Appl. No.: 15/257,885

(22) Filed: Sep. 6, 2016

(65) Prior Publication Data

US 2017/0086683 A1    Mar. 30, 2017

Related U.S. Application Data

(63) Continuation of application No. 13/596,923, filed on Aug. 28, 2012, now Pat. No. 9,433,515, which is a
(Continued)

(51) Int. Cl.
*A61B 5/02* (2006.01)
*A61B 5/0215* (2006.01)
(Continued)

(52) U.S. Cl.
CPC ............ *A61B 5/02035* (2013.01); *A61B 5/01* (2013.01); *A61B 5/0215* (2013.01); *A61B 5/055* (2013.01);
(Continued)

(58) Field of Classification Search
CPC ................. A61F 2250/0042; A61F 2210/0014
See application file for complete search history.

(56) References Cited

U.S. PATENT DOCUMENTS

| 4,665,906 A | 5/1987 | Jervis ............................. 128/92 |
| 4,733,665 A | 3/1988 | Palmaz ........................ 128/343 |

(Continued)

FOREIGN PATENT DOCUMENTS

| EP | 0 759 730 | 2/1999 | ............... A61F 2/06 |
| JP | 61-088135 | 5/1986 | ............. G01N 27/30 |

(Continued)

OTHER PUBLICATIONS

Anderson, et al., "Coatings for Blood Contacting Devices" *Medical Plastics and Biomaterials* pp. 1-9 (1998).
(Continued)

*Primary Examiner* — Jacqueline Woznicki
(74) *Attorney, Agent, or Firm* — David G. Rosenbaum; Benjamin D. Rotman; Rosenbaum IP, P.C.

(57) ABSTRACT

Implantable in vivo sensors used to monitor physical, chemical or electrical parameters within a body. The in vivo sensors are integral with an implantable medical device and are responsive to externally or internally applied energy. Upon application of energy, the sensors undergo a phase change in at least part of the material of the device which is then detected external to the body by conventional techniques such as radiography, ultrasound imaging, magnetic resonance imaging, radio frequency imaging or the like. The in vivo sensors of the present invention may be employed to provide volumetric measurements, flow rate measurements, pressure measurements, electrical measurements, biochemical measurements, temperature, measurements, or measure the degree and type of deposits within the lumen of an endoluminal implant, such as a stent or other type of endoluminal conduit. The in vivo sensors may also be used
(Continued)

therapeutically to modulate mechanical and/or physical properties of the endoluminal implant in response to the sensed or monitored parameter.

7 Claims, 2 Drawing Sheets

Related U.S. Application Data continuation of application No. 09/783,633, filed on Feb. 14, 2001, now Pat. No. 8,372,139.

(51) Int. Cl.

| A61F 2/91 | (2013.01) |
|---|---|
| A61F 2/82 | (2013.01) |
| A61B 5/1473 | (2006.01) |
| A61B 5/145 | (2006.01) |
| A61B 5/00 | (2006.01) |
| A61B 5/01 | (2006.01) |
| A61B 5/07 | (2006.01) |
| A61L 27/04 | (2006.01) |
| A61L 31/02 | (2006.01) |
| A61B 5/05 | (2006.01) |
| A61B 5/055 | (2006.01) |
| A61B 6/12 | (2006.01) |
| A61B 8/08 | (2006.01) |
| A61F 2/958 | (2013.01) |
| A61B 5/021 | (2006.01) |
| A61B 5/024 | (2006.01) |
| A61F 2/46 | (2006.01) |
| B23K 1/19 | (2006.01) |

(52) U.S. Cl.
CPC .......... *A61B 5/0507* (2013.01); *A61B 5/076* (2013.01); *A61B 5/1473* (2013.01); *A61B 5/4842* (2013.01); *A61B 5/6862* (2013.01); *A61B 5/6876* (2013.01); *A61B 6/12* (2013.01); *A61B 8/0841* (2013.01); *A61F 2/82* (2013.01); *A61F 2/91* (2013.01); *A61F 2/958* (2013.01); *A61L 27/04* (2013.01); *A61L 31/022* (2013.01); *A61B 5/02* (2013.01); *A61B 5/021* (2013.01); *A61B 5/02427* (2013.01); *A61B 5/145* (2013.01); *A61B 5/14503* (2013.01); *A61B 5/14532* (2013.01); *A61B 5/6846* (2013.01); *A61B 2562/0247* (2013.01); *A61B 2562/0276* (2013.01); *A61B 2562/12* (2013.01); *A61B 2562/164* (2013.01); *A61F 2002/4672* (2013.01); *A61F 2210/0014* (2013.01); *A61F 2210/0023* (2013.01); *A61F 2210/0042* (2013.01); *A61F 2210/0076* (2013.01); *A61F 2250/0001* (2013.01); *A61F 2250/0004* (2013.01); *A61F 2250/0014* (2013.01); *A61F 2250/0018* (2013.01); *A61F 2250/0029* (2013.01); *A61F 2250/0035* (2013.01); *A61F 2250/0042* (2013.01); *A61F 2250/0067* (2013.01); *A61F 2250/0068* (2013.01); *A61F 2250/0096* (2013.01); *A61F 2250/0098* (2013.01); *A61F 2310/00023* (2013.01); *B23K 1/19* (2013.01)

(56) References Cited

U.S. PATENT DOCUMENTS

| 4,935,345 | A | 6/1990 | Guilbeau et al. ............. 435/14 |
|---|---|---|---|
| 5,061,914 | A | 10/1991 | Busch et al. .................. 337/140 |
| 5,084,151 | A | 1/1992 | Vallana et al. ............ 204/192.11 |
| 5,133,845 | A | 7/1992 | Vallana et al. ............ 204/192.15 |
| 5,190,546 | A | 3/1993 | Jervis .............................. 606/78 |
| 5,346,508 | A | 9/1994 | Hastings ......................... 607/99 |
| 5,358,615 | A | 10/1994 | Grant et al. ............. 204/192.15 |
| 5,370,684 | A | 12/1994 | Vallana et al. .................... 623/1 |
| 5,411,551 | A | 5/1995 | Winston et al. ................. 623/1 |
| 5,540,828 | A | 7/1996 | Yacynych ..................... 204/418 |
| 5,562,641 | A | 10/1996 | Flomenblit et al. .......... 604/281 |
| 5,591,197 | A | 1/1997 | Orth et al. .................... 606/198 |
| 5,597,378 | A | 1/1997 | Jervis ............................ 606/78 |
| 5,597,458 | A | 1/1997 | Sanchez, Jr. et al. ..... 204/192.3 |
| 5,601,593 | A * | 2/1997 | Freitag ...................... A61F 2/90 606/191 |
| 5,649,952 | A | 6/1997 | Lam ............................. 606/198 |
| 5,749,880 | A | 5/1998 | Banas et al. ................. 606/198 |
| 5,797,898 | A | 8/1998 | Santini, Jr. et al. ......... 604/890.1 |
| 5,833,603 | A | 11/1998 | Kovacs et al. ............... 600/317 |
| 5,837,446 | A | 11/1998 | Cozzette et al. ................. 435/6 |
| 5,837,454 | A | 11/1998 | Cozzette et al. ................. 435/6 |
| 5,858,801 | A | 1/1999 | Brizzolara .................... 436/518 |
| 5,861,027 | A * | 1/1999 | Trapp ......................... A61F 2/91 606/191 |
| 5,865,801 | A | 2/1999 | Houser ............................ 604/96 |
| 5,866,113 | A | 2/1999 | Hendriks et al. ............ 424/78.17 |
| 5,874,047 | A | 2/1999 | Schoning et al. ............ 422/82.02 |
| 5,880,552 | A | 3/1999 | McGill et al. ............. 310/313 R |
| 5,914,026 | A | 6/1999 | Blubaugh, Jr. et al. ....... 205/792 |
| 5,922,183 | A | 7/1999 | Rauh ............................ 204/403 |
| 5,932,953 | A | 8/1999 | Drees et al. .................. 310/324 |
| 5,964,993 | A | 10/1999 | Blubaugh, Jr. et al. ....... 204/403 |
| 5,967,986 | A | 10/1999 | Cimochowski et al. ..... 600/454 |
| 5,976,466 | A | 11/1999 | Ratner et al. ............... 422/82.11 |
| 6,004,441 | A | 12/1999 | Fujiwara et al. ............. 204/412 |
| 6,007,298 | A | 12/1999 | Karem ............................ 416/44 |
| 6,016,693 | A | 1/2000 | Viani et al. ..................... 73/105 |
| 6,017,775 | A | 1/2000 | Igel et al. ....................... 438/48 |
| 6,030,827 | A | 2/2000 | Davis et al. ................ 435/287.1 |
| 6,053,873 | A | 4/2000 | Govari et al. ................. 600/505 |
| 6,077,298 | A | 6/2000 | Tu et al. ...................... 623/1.19 |
| 6,091,980 | A | 7/2000 | Squire et al. ................ 600/381 |
| 6,103,033 | A | 8/2000 | Say et al. ..................... 156/73.1 |
| 6,140,740 | A | 10/2000 | Porat et al. .................... 310/322 |
| 6,187,037 | B1 * | 2/2001 | Satz ......................... A61K 51/12 600/3 |
| 6,231,516 | B1 | 5/2001 | Keilman et al. ............. 600/485 |
| 6,237,398 | B1 | 5/2001 | Porat et al. .................. 73/54.09 |
| 6,239,724 | B1 | 5/2001 | Doron et al. ............. 340/870.28 |
| 6,264,687 | B1 | 7/2001 | Tomonto ..................... 623/1.16 |
| 6,296,615 | B1 | 10/2001 | Brockway et al. ........... 600/486 |
| 6,315,708 | B1 * | 11/2001 | Salmon ...................... A61F 2/90 600/3 |
| 6,406,493 | B1 | 6/2002 | Tu et al. ...................... 623/2.37 |
| 6,442,413 | B1 * | 8/2002 | Silver .................. A61B 5/0031 600/345 |
| 6,485,507 | B1 | 11/2002 | Walak et al. ................. 623/1.15 |
| 6,610,087 | B1 | 8/2003 | Zarbatany et al. ........... 623/1.32 |
| 6,652,576 | B1 | 11/2003 | Stalker .......................... 623/1.18 |
| 6,840,956 | B1 | 1/2005 | Wolinsky et al. ............ 623/1.13 |
| 6,890,350 | B1 | 5/2005 | Walak .......................... 623/1.15 |
| 7,017,404 | B1 * | 3/2006 | Kain ...................... A61B 5/0215 73/146.5 |
| 2001/0026111 | A1 | 10/2001 | Doron et al. ................ 310/322 |
| 2002/0183721 | A1 | 12/2002 | Santini, Jr. et al. ......... 604/890.1 |
| 2003/0059640 | A1 * | 3/2003 | Marton ...................... A61F 2/91 428/544 |
| 2004/0260391 | A1 | 12/2004 | Santini, Jr. et al. ........... 623/1.42 |
| 2005/0186241 | A1 | 8/2005 | Boyle et al. .................. 424/423 |
| 2007/0255395 | A1 | 11/2007 | Pollock et al. ............... 623/1.36 |

FOREIGN PATENT DOCUMENTS

| JP | 06-343704 | 12/1994 | ............ A61M 29/02 |
|---|---|---|---|
| JP | 11-285538 | 10/1999 | ............... A61N 1/37 |
| JP | 2000-507142 | 6/2000 | ........... A61B 5/0265 |
| WO | WO 95/031945 | 3/1997 | ............... A61F 2/06 |
| WO | WO 98/029030 | 7/1998 | ............... A61B 5/02 |
| WO | WO 98/050773 | 11/1998 | |
| WO | WO 99/023977 | 5/1999 | ............... A61F 2/06 |

(56) References Cited

FOREIGN PATENT DOCUMENTS

| WO | WO 00/059370 | 10/2000 | ............... A61B 5/00 |
| WO | WO 01/019239 | 3/2001 | ............... A61B 5/00 |
| WO | WO 01/087137 | 11/2001 | |

OTHER PUBLICATIONS

Bauters, "Growth Factors as a Potential New Treatment for Ischemic Heart Disease" *Clin. Cardiol.* 20(Suppl. II): II-52-II-57 (1997).
Bertrand, et al., "Biocompatibility Aspects of New Stent Technology" *JACC* 32(3): 562-571 (1998).
Brem, "Angiogenesis and Cancer Control: From Concept to Therapeutic Trial" *Cancer Control Journal* 6(5): 1-28 (2000).
Fischer, "Continuous in vivo monitoring in diabetes" *Biosensors and Bioelectronics*, 10: xxiii (1995) http://dx.doi.org/10.1016/0956-5663(95)99256-K.
Frost and Sullivan, "World Biosensor Market" *Report* pp. 5326-5332 (1997).
Golightly, "Biosensors May Revolutionize Space Life Support" pp. 1-3 (Jan. 26, 2000).
Henry, "Getting Under the Skin: Implantable glucose sensors" *Anal. Chem* 70(17): 594A-598A (1998) http://pubs.acs.org/doi/abs/10.1021/ac981937%2B.
Hernandez, et al., "Human Endothelial Cell Cultures from Progenitor Cells Obtained by Leukapheresis" *Southeastern Surgical Congress* pp. 1-8 (2000).
Hodgson, et al., "Shape Memory Alloys" *Shape Memory Applications, Inc.* pp. 1-11 (1999).
IBM, "IBM and University Researchers Uncover New Biomechanical Phenonmenon Using Tiny Silicon 'Fingers,'" http://monet.physik.unibas.ch/nose/biosensor pp. 1-6 (Apr. 14, 2000).
Isner, et al. "Therapeutic Angiogenesis" *Frontiers in Bioscience* 3: 49-69 (May 5, 1998).
Jacobson, "Biosensors and Other Medical and Environmental Probes" pp. 1-15 (2000).
Kumar, "Biosensors Based on Piezoelectric Crystal Detectors: Theory and Application," *JOM-e* 52(10): 1-9 (2000) http://www.tms.org/pubs/journals/JOM/0010/Kumar/Kumar-0010.html.
Lal, et al., "Non-invasive Ultrasound Induced Heating of Stents: Importance of Stent Composition" (2000).
Lowe, "Biosensors and Bioelectronics" *The University of Cambridge Institute of Biotechnology* pp. 1-2 (Mar. 2000).
Mentz, et al., "Solid State Biosensors" *Spring 1998 MSE 4206 Project* pp. 1-30 (Apr. 27, 1998).
Naguib, et al., "Stent diathermy using focused ultrasound and microwave" http://www.hotplague.com/frames_abstracts/rabs3.htm.
Owens, "Preliminary Design of an Implantable Biosensor for the Detection and Differentiation of Acute Rejection, Vascular Occlusion, and Infection in the Liver or Kidney Transplant Graft" *Thesis Abstract* pp. 1 (Jun. 2000).
Pedram, et al., "Vasoactive peptides modulate vascular endothelial cell growth factor production and endothelial cell proliferation and invasion" *J. Biol Chem* 272(27): 17097-103 (1997).
Pohan, et al., "An Introduction to Biosensors" *Rensselaer Polytechnic Institute* pp. 1-2 (1995).
Randert, D., et al., "Magnetic Resonance compatibility of Ni—Ti Stents" Abstract 8.P1, SMST-97 Conference (International Organization on Shape Memory and Superelastic Technologies), http://www.fwsystems.com/professional/smstabs.html.
Rajabi, et al., "MRI Detecion of Atherosclerotic Vulnerable Plaque Using Super Paramagnetic Iron Oxide (SPIO) Contrast Media" Abstract published for presentation at the ACC 2001, the American College of Cardiology Scientific Session, Mar. 18-21, 2001.
Reneman, et al., "Noninvasive vascular ultrasound: An asset in vascular medicine" *Cardiovascular Research* 45: 27-35 (2000).
Rizzo, et al., "Rapid Mechanotransduction in Situ at the Luminal Cell Surface of Vascular Endothelium and its Caveolae" *Journal of Biological Chemistry* 273(41): 26323--26329 (Oct. 9, 1998).
Seely, "The Future of Medical Microeletrcomechanical Systems" *MEM* (1996).
Spera, "Biosensor Research Targets Medical Diagnostics" *R&D Horizons* pp. 1-9 (Nov. 11, 1997).
Stables, et al., "Advances in Coronary Stenting" *JACC, Journal Review* (May/Jun. 1998) pp. 27-30.
Stone, "Advanced Biosensors Promise to Fight Disease" *NIE, 71.2* pp. 1-3 (Aug. 1999).
Turner, "Biosensors: Past, Present, and Future" *Essays in Biotechnology* pp. 1-7 (1996).
Weetall, "Nano-and MEMS Technologies for Chemical Biosensors: Program Overview" *Advanced Technology Program NIST* pp. 1-2 (1998).
1992, 64, 148 IUPAC Compendium of Chemical Terminology 2nd Edition (1997).
"AHA Abstract Viewer Search Results".
"Biomaterial Research: Enhancing the quality of life," *STNEWS* pp. 1-9 (1998).
"Biosensors and Biochips," www.oml.gov/virtual/biosensors pp. 1-2 (2000).
"Biosensors Defined," *Environmental Science and Technology* pp. 1 (1996).
"Biosensors" *USCSD Department of Chemistry and Biochemistry* pp. 1-2 (2000).
"Continuous Monitoring of Blood Glucose Levels," www.animascrop.com/sensor_f.html pp. 1-3 (Mar. 6, 2000).
"Fighting Diabetes: UD researchers move closer to chip-based control of 'smart,' implantable insulin pumps" *University of Delaware*, http://www.sciencedaily.com/releases/1999/06/990608071652.htm, pp. 1-3 (Jun. 6, 1999).
"First Annual Beacon Symposium: 'Biosensors,'" *The Biomedical Engineering Alliance for Connecticut (BEACON)* pp. 1-13 (1998).
"Glossary of NiTi Terminology" www.sma-inc.com/glossary.htm pp. 1-2 (1999).
"Gluco Watch: One Step Closer," http://diabetes.about.com/health/diabetes/library/weekly/aa121099.htm pp. 1-5 (Dec. 10, 1999).
"Glucose Biosensor" *Synthetic Blood International, Inc., Press Release* pp. 1-2.
"Introduction to Sensors" *The National Academy of the Sciences* pp. 9-17 (1995, 2000).
"ISSYS Crafts MEMS Devices to Advance Real-World Systems Applications" *Sensor Business Digest, Sensor Industry Developments and Trends*, Apr. 2000 pp. 1-7.
"MEMS Could Unlock Door to Early Diagnosis, Intervention in Cardiovascular Disease" *CUT Technology* pp. 1-2 (Fall 1999).
"Micro Biological and Chemical Sensors" *Center for Microelectronic Sensors and MEMS* pp. 1 (May 25, 1997).
"Micro Flow and Pressure Sensors" *Center for Microelectronic Sensors and MEMS*, www.mems.uc.edu/research/r101.htm. pp. 1 (Oct. 17, 2000).
"Novel Imaging Modalities" *Transcatheter Cardiovascular Therapeutics Poster Abstracts* pp. 271-284 (2000).
"S.C.A.N. Individual Microchip Technology, Frequently Asked Questions (FAQ)" *Microchip Technology* pp. 1-24 (2000).
"Sensor Technology" *Technical Insights, John Wiley & Sons, Inc.* pp. 1-2 (1997).
"Sensors and Sensor Systems" *Sensors and Technology* pp. 1-10.
"Synthetic Blood International Announces New Glucose Biosensor Development Program with UMM Electronics" *Press Release* pp. 1-2 (Aug. 7, 2000).
"Transformation Temperature Hysteresis in NiTi Alloys" *Shape Memory Applications, Inc.* pp. 1-2 (1999).

* cited by examiner

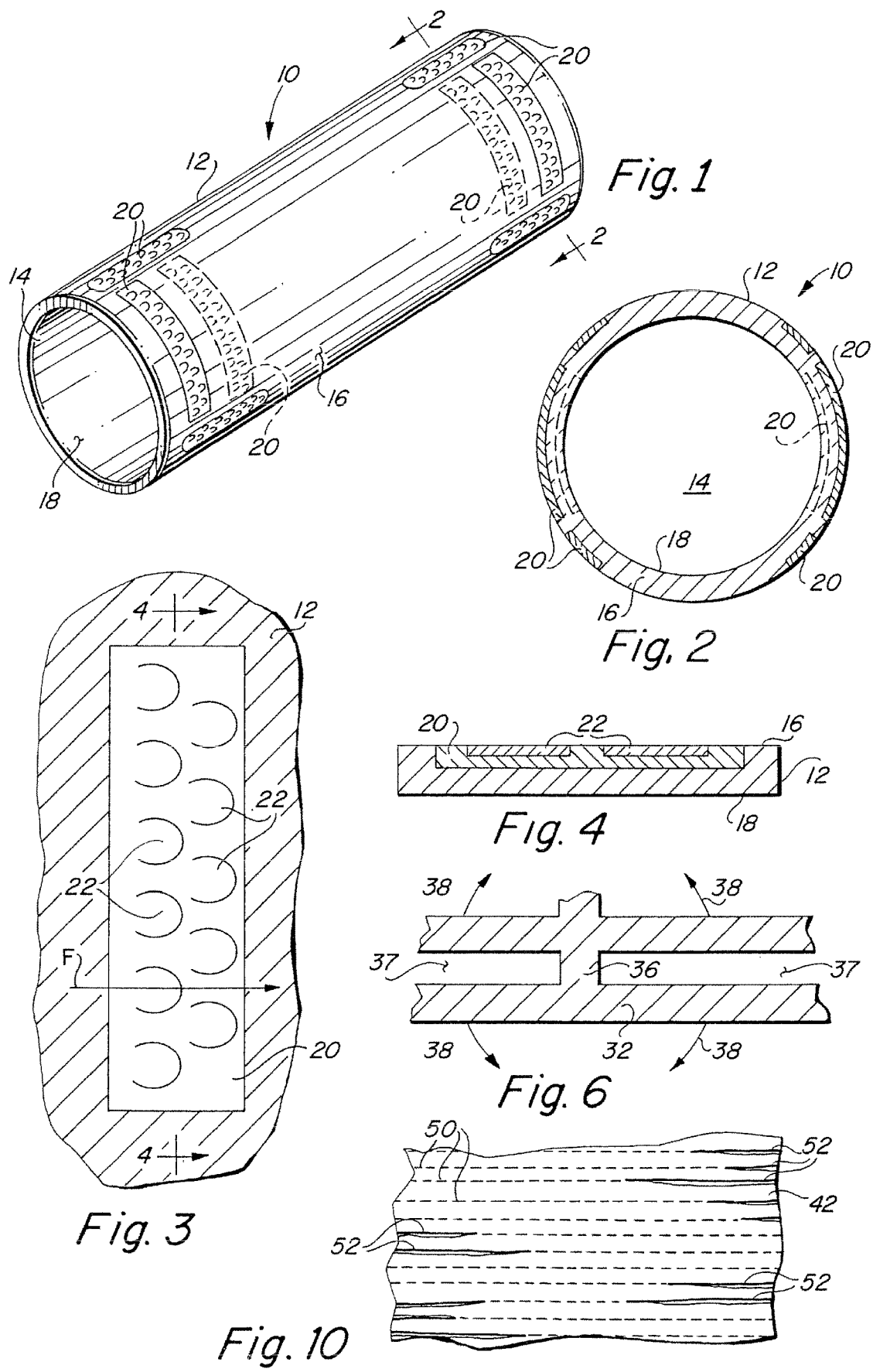

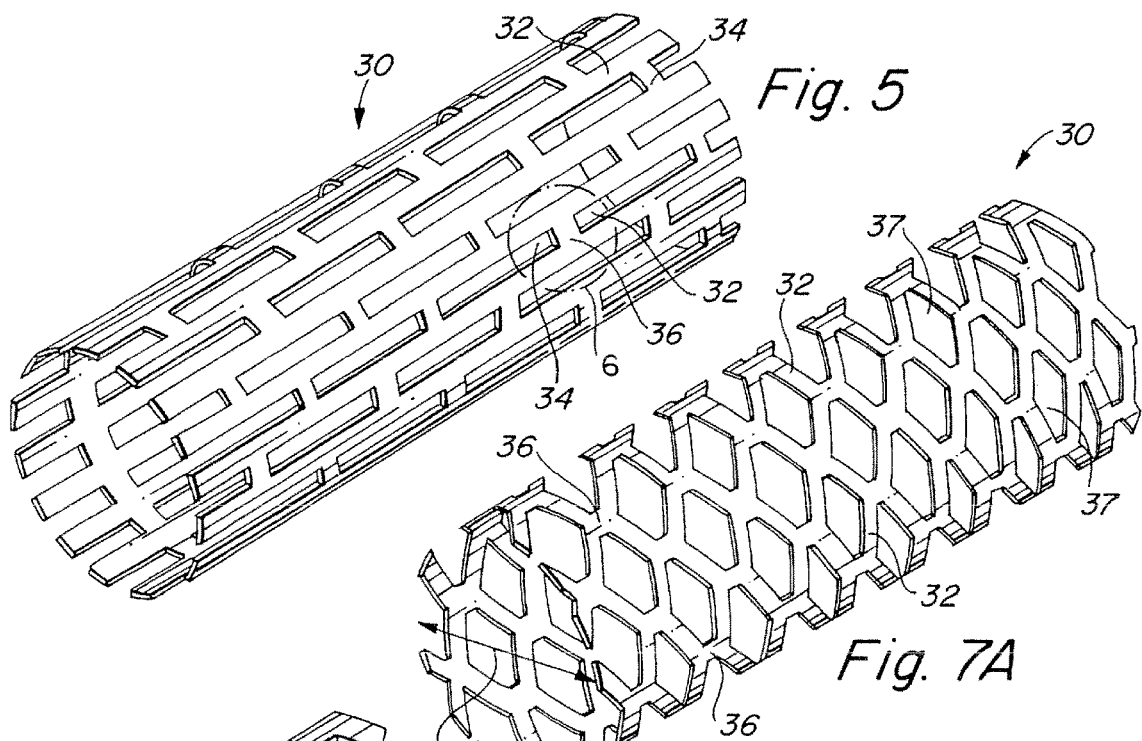
Fig. 5
Fig. 7A
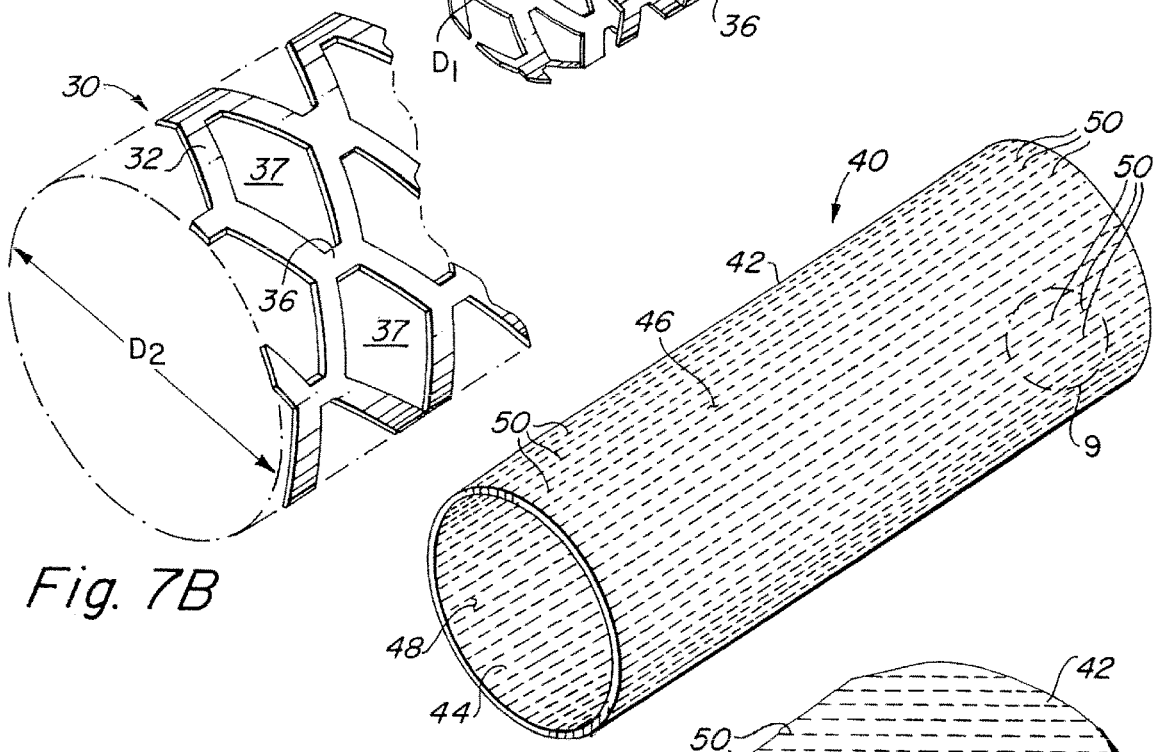
Fig. 7B
Fig. 8
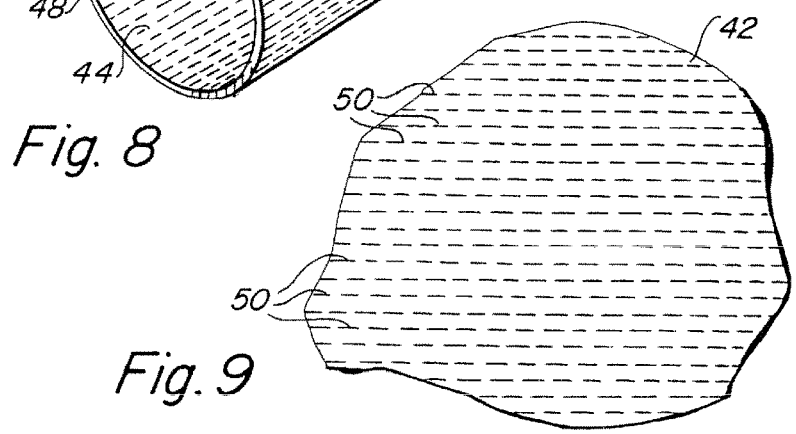
Fig. 9

METHOD OF USING AN IN VIVO SENSOR HAVING DIFFERENTIAL MATERIAL PROPERTIES

CROSS-REFERENCE TO RELATED APPLICATIONS

This is a continuation of commonly assigned U.S. patent application Ser. No. 13/596,923, filed Aug. 28, 2012; which is a continuation of U.S. patent application Ser. No. 09/783,633, filed Feb. 14, 2001, now U.S. Pat. No. 8,372,139, which are hereby incorporated by reference in their entirety.

BACKGROUND

The present invention relates generally to the field of implantable medical devices, and more particularly pertains to sensors that may be implanted into a body to elicit at least one of a mechanical, chemical or electrical response to an in vivo physiological condition or state with the body.

Post-implantation evaluation of the patency of an endoluminal device presently requires clinical examination by angiography or ultrasound. The results of these tests provide a qualitative evaluation of device patency. It is, therefore, desirable to provide a means for quantitatively measuring the post-implantation patency of an endoluminal device on either a periodic or continuous basis. Quantitative in vivo measurements of volumetric flow rate, flow velocity, biochemical constitution, fluid pressure or similar physical or biochemical property of the body fluid through an endoluminal device would provide more accurate diagnostic information to the medical practitioner.

As used herein, the term "endoluminal device" is intended to include stents, grafts and stent-grafts which are implanted within an anatomical passageway or are implanted with a body to create a non-anatomical passageway between anatomically separated regions within the body. Endoluminal devices in accordance with the present invention may include endovascular devices, prostatic devices, urethral devices, cervical devices, esophageal devices, intestinal devices, biliary devices, intra-cardiac devices, valves, hepatic devices, renal devices or devices with similar application within the body.

The term "sensor," as used in this application, is intended to include, without limitation, biosensors, chemical sensors, electrical sensors and mechanical sensors. While the term "biosensor" has been used to variously describe a number of different devices which are used to monitor living systems or incorporating biological elements, the International Union for Pure and Applied Chemistry (IUPAC) has recommended that the term "biosensor" be used to describe "a device that uses specific biochemical reactions mediated by isolated enzymes, immunosystems, tissues, organelles or whole cells to detect chemical compounds usually by electrical, thermal or optical signals" 1992, 64, 148 IUPAC Compendium of Chemical Terminology 2nd Edition (1997). The term "chemical sensor" is defined by the IUPAC as a device that transforms chemical information, ranging from concentration of a specific sample component to total composition analysis, into an analytically useful signal. Conventional biosensors are a type of chemical sensor that consists of three basic elements: a receptor (biocomponent), transducer (physical component) and a separator (membrane or coating of some type). The receptor of a chemical sensor usually consists of a doped metal oxide or organic polymer capable of specifically interacting with the analyte or interacting to a greater or lesser extent when compared to other receptors. In the case of a biosensor the receptor or biocomponent converts the biochemical process or binding event into a measurable component. Biocomponents include biological species such as: enzymes, antigens, antibodies, receptors, tissues, whole cells, cell organelles, bacteria and nucleic acids. The transducer or physical component converts the component into a measurable signal, usually an electrical or optical signal. Physical components include: electrochemical devices, optical devices, acoustical devices, and calorimetric devices as examples. The interface or membrane separates the transducer from the chemical or biocomponent and links this component with the transducer. They are in intimate contact. The interface separator usually screens out unwanted materials, prevents fouling and protects the transducer. Types of interfaces include: polymer membranes, electropolymerized coatings and self-assembling monomers.

Sensors should have high selectivity and sensitivity, have rapid recovery times with no hysteresis, long lifetimes if not single use, low drift, automated calibration, self-diagnostic, low cost, no reagent additions required and no sample preparation. It is obvious that presently available chemical sensors and biosensors do not meet these criteria (World Biosensor Market, Frost and Sullivan, Report 5326-32, 1997). National Institute of Standards and Technology, Nano-and MEMS Technologies for Chemical Biosensors, (www.atp.nist.gov/atp/focus/98wp-nan.htm).

In the clinical diagnostic market, various sensor designs are known including electrochemical sensors (potentiometric ISEs; amperometric; conductometric; miniaturized ISEs; field effect transistors; interdigitated transistors); optical sensors using fiber-optic or surface plasmon resonance technologies; acoustic sensors such as piezo-crystal and surface acoustic wave sensors; and thermal sensors which employ thermistors. Thus, it is known to employ microfabrication techniques to make clinical sensors. Currently, the most commercially successful microfabricated sensor in the clinical diagnostic market is the MEDISENSE glucose meter that uses an electrochemical transduction of an enzymatic reaction. However, the need for in vivo sensing systems is well recognized. Work on in vivo sensing systems for both glucose and lactate has confirmed the effectiveness of phospholipid copolymers in improving hemocompatibility. Fisher, U., et al. Biosen. Bioelectron., 10, xxiii (1995).

By their nature, implantable sensors must have some mechanism for communicating sensed information from the sensor to a reader, which may be human or machine, outside the body. Since it is impractical to implant a physical connection between the sensor and the external reader, alternative means for generating a readable signal external the body must be provided. Suitable means for generating a readable signal external the body include, without limitation, radiographically visible signals, magnetic flux signals, chemical signals, chemifluorescent signals, and/or electrical signals.

The pathogenesis of arteriosclerosis has not been positively identified. A number of risk factors, such as high cholesterol, hypertension, and diabetes are known to serve to turn on inflammatory mechanisms at the arterial wall and recruit white cells into the arterial wall to ultimately cause the formation and breakdown of plaque, which, in turn, lead to clinical events. The process starts out with oxidation-sensitive nuclear regulatory mechanisms. Free radicals control the genes that cause the synthesis of proteins that are expressed in the endothelial cells and serve to attract white cells into the arterial wall.

Endothelialization of an implanted medical device has been the subject of considerable scientific study and literature. It is know known that various growth factors and cytokines are responsible for activating smooth muscle cell receptors and initiating smooth muscle cell proliferation. Endothelial cell growth factors such as fibroblast growth factor (FGF) and vascular endothelial growth factor (VEGF) have been identified as significant for endothelial cell growth in vitro. While VEGF is specific for endothelial cells, FGFs also stimulate smooth muscle cell growth. Bauthers, C., Growth Factors as a Potential New Treatment for Ischemic Heart Disease, Clin. Cardiol. 20:11-52-11-57 (1997).

It has been recognized that there is a need for an in vivo sensor capable of sensing binding of endothelial cells or arterioschlerotic plaque, and providing an ex vivo detectable signal, without requiring external or internal power sources.

SUMMARY OF THE INVENTION

In accordance with the present invention, there is provided an implantable in vivo sensor suitable for monitoring clinically significant physiological events. The present invention provides an integrated device which is implantable within an anatomical passageway, such as a blood vessel, in the esophageal or gastro-intestinal tract, bile duct, hepatic duct, within the renal system, such as within a ureter or urethra, vagina or cervix, vas deferens, bronchi or similar anatomical passageways; within an organ, or within an anatomical defect, such as a cardiac septal defect.

The inventive in vivo sensor consists generally of an implantable substrate carrier element and at least one of a plurality of sensor elements. The implantable substrate carrier element may consist of, for example, a stent, stent-graft, graft, valve, filter, occluder or other implantable medical device, which serves as a foundational element for the sensor elements. Under conditions where the implantable substrate carrier, itself, is configured to return a detectable signal, the implantable carrier element, itself, may constitute the sensor element. Where the implantable substrate carrier element and the sensor element are discrete, conjoined elements, they may be fabricated of like materials or of dissimilar materials, each having either similar or dissimilar thermal, mechanical, electrical and/or chemical properties.

Microfabrication techniques are preferably employed to create both the carrier element and the sensor element in such a manner that both the substrate carrier element and the sensor element have a defined geometry and conformation that is suitable for use as a thermal, electrical, mechanical or chemical sensor, for sensing, for example, fluid flow, fluid flow rate, or fluid pressure in the region of the sensor. The addition of chemical or biological compounds to inventive sensor permits the device to be used as either a chemical or a biosensor, respectively. Similarly, microelectronic circuits may be added to the inventive sensor, such as by fabricating integrated circuits into or onto the inventive sensor, to enable the sensor to detect electrochemical events occurring at the sensor, such as arteriosclerotic plaque being deposited onto the surface of the sensor, or to detect electrochemical changes in the anatomical environment into which the sensor is implanted.

Alternatively, the inventive implantable sensor element and the implantable substrate carrier element may be fabricated of wrought materials, such as stainless steely hypotubes, stainless steel wire, shape memory hypotubes and shape memory wires. The sensor element may be attached to the substrate carrier element, or component parts, such as cantilever members, of the sensor element may be attached to the sensor element by a variety of known means. For example, welding processes may be used, such as laser welding, plasma welding, resistance welding, or e-beam welding. Welding, however, is generally not an acceptable method for joining nickel-titanium alloys to other materials, e.g., stainless steel, because brittle intermetallics may be formed in the weld zone. In order to obtain a weld that is free of oxides or nitrides, welding should be performed under stringent environmental conditions in a clean, inert atmosphere or in vacuum in order to minimize reactivity of the titanium. In some cases, welded nickel-titanium parts may require heat-treating after welding to stress relieve the weld zone. The heat-affected zone will generally not exhibit superelastic properties. Soldering may be employed to join shape memory or superelastic alloys, such as nitinol, to stainless steel and other materials. However, a proper flux must be selected which inhibits the formation of surface oxides during the soldering process. Ultrasonic soldering has also been used to try to keep the surface free of oxides during soldering. Various epoxies and other adhesives may be used to join shape memory alloys either to themselves or to other materials. The chosen adhesives must, of course, be compatible with both the manufacturing and in vivo biological environments of the device. Finally, the sensor element may be mechanically joined to the substrate carrier element, or component parts of the sensor element maybe joined together by crimping, providing an interference fit or by creating interlocking geometries of the sensor element or its component parts.

In accordance with a particular embodiment of the present invention, an endoluminal implant is provided which is implantable within an anatomical or non-anatomical body passageway to determine a given condition of a fluid flow through the endoluminal implant within the body passage. The inventive endoluminal implant may include, for example, an endoluminal stent, stent graft, or graft that consists of a generally tubular shaped member having two diametric states. In order to facilitate transluminal catheter introduction, the inventive endoluminal device has a first diametric state in which the transverse cross-sectional area of the device is of sufficient size to permit percutaneous introduction and in vivo placement of the device using transluminal approaches. A second diametric state has a transverse cross-sectional area which is larger than the first diametric state and conforms to the diameter of the anatomical passageway into which the device is placed, or is of a desired diameter for non-anatomical passageways. The inventive endoluminal device may be fabricated as a balloon expandable device, a self-expanding device, a shape-memory device or a superelastic device. It will be understood by those of skill in the art that the term "balloon expandable" refers to a class of devices which rely upon application of an external pressure, such as that applied by a balloon catheter, to radially deform the device from its first diametric state to its second diametric state; that the term "self-expanding" refers to a class of devices which rely upon the inherent mechanical properties of the device material to expand the device from its first diametric state to its second diametric state; that the term "shape-memory" refers to a class of devices which are fabricated of materials which exhibit martensitic phase transformation at certain transition temperatures; and the term "superelastic" refers to a class of devices which are fabricated of materials which deform under given stress-strain conditions. The inventive endoluminal sensor may be fabricated of materials capable of undergoing elastic or plastic deformation, such as stainless steel, tantalum, titanium, gold, or other biocompatible metals. However, the present invention is preferably fabricated of a shape-memory and/or superelastic material, such as nickel-titanium alloys known as Nitinol, which are mechanically responsive to temperature changes and/or changes in applied stress or strain, respectively.

Generally, the inventive endoluminal sensor consists of a sensor which is integral with an implantable endoluminal device, such as stent, and which is configured to respond either mechanically, electronically, electromechanically, or chemically, to cause a mechanical, electrical, electromechanical or chemical change at the sensor and/or the endoluminal device which is detectable ex vivo using non-invasive detection methodologies such as radiography, ultrasonography, magnetic resonance imaging, or radio frequency detection.

In accordance with one embodiment of the invention, the inventive sensor comprises at least one integral region of the implantable endoluminal device that is formed as a plurality of cantilever members fabricated of shape-memory materials having different transformation temperatures. The sensor may be positioned on either a fluid contacting or tissue-contacting surface of the implantable device, such as the luminal surface of a stent which contacts blood, or on the abluminal surface of a stent which contacts neointimal tissue of the blood vessel. Alternatively, the sensors may be positioned on both the fluid contacting and the tissue-contacting surface of the implantable device. The present invention provides a vacuum deposited film which may be either a monolithic monolayer of material or a multilayered film having at least portions of the film capable of sensing at least one of changes in temperature, pressure, or the presence or absence of chemical or biochemical species in the body by mechanical, electrical, chemical, electrochemical or electromechanical means.

Specifically, the present invention relates to the manufacture and use of implantable sensors to monitor physical, chemical or electrical parameters of a fluid flow through a body passageway. For example, the sensors of the present invention may be employed to provide volumetric measurements, flow rate measurements, pressure measurements, electrical measurements, biochemical measurements, temperature, measurements, or measure the degree and type of deposits within the lumen of an endoluminal implant, such as a stent or other type of endoluminal conduit. The present invention also provides a means to modulate mechanical and/or physical properties of the endoluminal implant in response to the sensed or monitored parameter. For example, where the monitored blood flow volume through an endoluminal device is determined to be below physiological norms and/or the blood pressure is determined to be above physiological norms, the stent may be actuated to increase its diameter, such as by superelastic properties of the stent materials.

BRIEF DESCRIPTION OF THE DRAWINGS

In the accompanying figures, like elements are identified by like reference numerals among the several preferred embodiments of the present invention.

FIG. 1 is a perspective view of an endoluminal implant in accordance with the present invention.

FIG. 2 is a cross-sectional view taken along line 2-2 of FIG. 1.

FIG. 3 is a fragmentary plan view of a first embodiment of the present invention illustrating an integral sensor formed of a plurality of cantilever members.

FIG. 4 is a cross-sectional view taken along line 4-4 of FIG. 3.

FIG. 5 is a perspective view of an endoluminal implant in accordance with a second embodiment of the present invention.

FIG. 6 is a fragmentary plan view of a diametrically adjustable region of the second embodiment of the present invention.

FIG. 7A is a perspective view of the second embodiment of the inventive endoluminal implant of the present invention in its diametrically reduced state.

FIG. 7B is a perspective view of the second embodiment of the inventive endoluminal implant of the present invention in its diametrically expanded state.

FIG. 8 is a perspective view of a third embodiment of the inventive endoluminal implant of the present invention depicting weakened regions in the bulk material in phantom.

FIG. 9 is a fragmentary enlarged plan view of circled region 9 in FIG. 8.

FIG. 10 is a fragmentary plan view illustrating propagation of a microgroove upon binding of an endothelial cell to a binding domain at the weakened region in the bulk material of the third embodiment of the present invention.

DETAILED DESCRIPTION OF THE INVENTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

To simplify description of the present invention, most of the preferred embodiments will be described with reference to an endoluminal stent, except where otherwise stated. However, those of ordinary skill in the art will understand that each embodiment has application to a variety of implantable devices including, without limitation, stents, grafts, stent-grafts, valves, shunts or patches.

As used herein, the term "integral" is intended to include regions that are formed as a part of the bulk material of the endoluminal device and regions which are formed separately from the bulk material of the endoluminal device, but which are coupled thereto.

In accordance with another embodiment of the invention, the inventive sensor comprises at least one region of the implantable endoluminal device that is formed of a plurality of cantilever members having different mechanical properties, such as different modulus of elasticity, plasticity or stress-strain behaviors. In accordance with the best mode presently contemplated for the invention, the cantilever members are preferably fabricated of a superelastic material. As with the shape-memory cantilever members, the superelastic cantilever members may be positioned on either a fluid contacting or tissue contacting surface of the implantable device, such as the luminal surface of a stent which contacts blood, or on the abluminal surface of a stent which contacts neointimal tissue of the blood vessel. Alternatively, the sensors may be positioned on both the fluid contacting and the tissue-contacting surface of the implantable device. Unlike the shape-memory cantilever sensors, the superelastic cantilever sensors are responsive to changes in force, such as shear forces, applied to the sensors.

With both the shape-memory cantilever members sensor and the superelastic cantilever members sensor, each of the plurality of cantilever members have first and second positions that are indicative of either an off or on position, respectively. The first or "off" position of each cantilever members is coplanar or flush with the surface of the endoluminal device into which the sensor is positioned. In the second or "on" position, each activated cantilever members projects outwardly from the surface of the endoluminal device into which the sensor is positioned. Because different cantilever members or groups of cantilever members are fabricated to have either different transition temperatures or different stress-strain properties, individual cantilever members or groups of cantilever members which are in the second or "on" position, are indicative of a given thermal or stress-strain condition existing within the body into which the endoluminal device is implanted.

In one particular form of the invention, the inventive endoluminal device comprises a temperature sensor having a plurality of cantilever members positioned on at least one of the proximal, distal or intermediate regions of the endoluminal device and positioned on at least one of the luminal or abluminal wall surfaces of the endoluminal device. To facilitate ease of detection, a plurality of groups of cantilever members are provided, each group is formed of a plurality of individual cantilever members, with each individual cantilever members in the group having identical transition temperatures. The plurality of groups of cantilever members are arrayed along the longitudinal axis of the endoluminal device in such a manner as to create a continuum of groups of cantilever members having different transition temperatures. Changes in temperature at the site of the endoluminal device are indicated by the position of the cantilever members or groups of cantilever members as determined by radiography, ultrasonography, magnetic resonance imaging or other means that provides a detectable image of the position of the cantilever members and groups of cantilever members.

In another particular form the invention, the sensor comprises a plurality of cantilever members positioned on at least one of the proximal, distal or intermediate regions of the endoluminal device and positioned on at least one of the luminal or abluminal wall surfaces of the endoluminal device. To facilitate ease of detection, a plurality of groups of cantilever members are provided, each group is formed of a plurality of individual cantilever members, with each individual cantilever members in the group having identical transition temperatures. The plurality of groups of cantilever members are arrayed along the longitudinal axis of the endoluminal device in such a manner as to create a continuum of groups of cantilever members having different stress-strain transition pressures. Changes in applied stress or strain, such as blood pressure or blood flow shear stress, at the site of the endoluminal device are indicated by the stress and strain acting on the cantilever members or groups of cantilever members which provides a corresponding frequency shift in energy reflected, when compared to a baseline stress-strain for unloaded cantilever members. The position and frequency shift of the cantilever members may be determined by radiography, ultrasonography, magnetic resonance imaging or other means which provides a detectable image of the position of the individual cantilever members and groups of cantilever members or is capable of measuring frequency shifts due to differential stress-strain loading onto the cantilever members.

In yet another form of the invention, the inventive sensor is a biosensor that is microfabricated from a material capable of undergoing elastic, plastic, shape-memory or superelastic deformation, and has a plurality of cantilever members formed therein, as described above. Each of the plurality of cantilever members has at least one binding domain selective for at least one indicator of endothelialization selected from the group of endothelial cell surface proteins, antigens, antibodies, cytokines, growth factors, co-factors, or other biological or biochemical marker of endothelial cells or endothelial cell precursors. Binding of the at least one indicator to at least one of the plurality of cantilever members causes a change in strain applied to the cantilever members, thereby causing the relevant cantilever members or groups of cantilever members to undergo superelastic transformation from the first or "off" position to the second or "on" position. As with the above-described embodiments of the invention, the position of the sensor cantilever members in the second or "on" position relative to the endoluminal device is then detected and is indicative of the progress of endothelialization.

Similarly, the fact of or the progress of arterioschlerotic plaque formation may be sensed using a plurality of elastic or superelastic cantilever members. In accordance with a first embodiment, the plurality of superelastic cantilever members undergo martensitic transformation as a result of the strain applied to the cantilever members resulting from growth of arterioschlerotic plaque onto the cantilever members. In accordance with a second embodiment, the plurality of superelastic cantilever members has at least one binding domain selective for at least one indicator of arterioschlerotic plaque or its precursors. Binding of the arterioschlerotic plaque or precursors of arterioschlerotic plaque to the binding domain on the cantilever members, adds a quantum of strain to the cantilever members sufficient to cause the cantilever members to undergo superelastic transformation from the first or "off" position to the second or "on" position. As with the above-described embodiments of the invention, the position of the sensor cantilever members in the second or "on" position relative to the endoluminal device is then detected and is indicative of the progress of arteriosclerosis.

Yet another form of the invention entails an implant fabricated of a superelastic material that has a variable diametric geometry responsive to changes in pressure applied to the implant. This form of the invention is preferably employed as a smooth muscle prosthesis, for example, as a vascular prosthesis, and is responsive to blood pressure changes in a manner similar to those changes native to blood vessels, i.e., contracting upon sensing lowered blood pressures and expanding upon sensing higher blood pressures, in order to maintain physiologically normal blood pressure. In this embodiment of the invention, a tubular implant is fabricated, in whole or in part, of a superelastic material and has diametrically adjustable regions that undergo superelastic transformation to increase or decrease the diameter of the implant upon sensing given physiological pressures within the implant.

Finally, another form of the invention consists of an endoluminal implant similar to that described in co-pending, commonly assigned U.S. Patent Application Ser. No. 60/064,916, filed Nov. 7, 1997 which was published as PCT International Application WO9923977A1 entitled Intravascular Stent And Method For Manufacturing An Intravascular Stent, both of which are hereby incorporated by reference. In those applications there is described an endoluminal implant having a plurality of microgrooves on the luminal and/or abluminal surfaces thereof which facilitate improved endothelialization over a non-grooved endoluminal implant. In accordance with the present invention there is provided an endoluminal implant having a plurality of putative microgrooves comprising sections of weakened bulk material of the endoluminal implant. The endoluminal implant is preferably fabricated of a superelastic bulk material and weakened regions in the bulk material are formed using standard microlithographic techniques to form the putative microgrooves. A plurality of binding domains are created along the fluid flow surface of the endoluminal implant and at proximal (relative to the blood flow) regions of the putative microgrooves that preferentially bind to endothelial cell surface proteins. Binding of the endothelial cell surface proteins to the binding domains causes a shift in the applied strain to the superelastic bulk material, which causes the superelastic bulk material to deform in the region of the applied strain, thereby breaking the interatomic bonds in the weakened regions of the putative microgrooves and causing formation of a portion of a microgroove. Propagation of the endothelial cell proliferation along the surface of the superelastic bulk material causes, in turn, a propagation of strain along the superelastic bulk material that causes the formation of the microgrooves in the superelastic bulk material.

The particular means for detecting a change in the inventive sensor and/or the particular means for activating a change in the inventive sensor is generally not considered part of the present invention. For example, it is known that ultrasound energy may be employed to generate both one-way and two-way shape memory effects in nickel-titanium alloys. V. V. Klubovich, V. V. Rubanick, V. G. Dorodeiko, V. A. Likhachov, and V. V. Rubanick Jr. (Institute of Tech. Acoustics, 13 Ludnikova, 210026 Vitebsk, Belarus,) Generation of Shape Memory Effect in Ti—Ni Alloy by means for Ultrasound, Abstract 1.P12, SMST-97 conference found at URL http://www.fwsystems.com/professional/smstabs.html. Using ultrasound energy to non-invasively induce stent heating has also been confirmed by B. Lal, et al. in their abstract entitled Non-Invasive Ultrasound Induced Heating of Stents: Importance of Stent Composition, which may be found at URL http://www.hotplaque.com/frames/abstracts/rabs6.htm and URL http://ex2.excerptamedica.com/00acc/abstracts/abs1065-117.html. Lal, et al. hypothesized that gentle heating can be accomplished using ultrasound (US) and a constant temperature can be maintained using pulsed US. The heating rate of an object under the same US power and frequency is determined primarily by its absorption and reflection rates. To test their hypothesis, they used a phantom of 5.08 cm thick layer of pork muscle, in which various annular stent shape materials were placed. To monitor the heating multiple hypodermic thermocouples were used. The heating was induced using FDA-approved levels of therapeutic ultrasound (intensity 0.5-2.5 W/cm.sup.2, frequency 1-3 MHz) in both pulse and continuous modes. It was found that nylon, and some types of PVC, exhibit temperature increases that are larger (2-35° C.) and faster (1.5-15 times) than the surrounding tissue, while Lexan, PTFE, Latex, Teflon, Ceramic and Delrina do not display selective heating. A modest heating effect (2° C. increase in 15 minutes) was also found in a metal stent. Lal, et al. concluded that ultrasound heating of tissue adjacent to a prosthesis depends on stent composition, induction of thermal apoptosis by ultrasound may prove to be effective in limiting restenosis in polymeric stents and grafts. Issues that need to be addressed include the optimal biocompatible material and design of stents and the in vivo effects of phased-array US on the stented artery and its surrounding tissues. Lal, et al. believed that by using fast-heating, non-toxic materials, ultrasound-heated stents could be devised.

Similarly, microwave radiation may be used to generate shape memory effects in shape memory alloys. It is known, for example, that microwave radiation may be used for stent diathermy in stainless steel stents. S. Naguib, et al. in Stent diathermy using focused ultrasound & microwave found at URL http://www.hotplaque.com/frames/abstracts/rabs3.htm sought to use ultrasound and microwave energy to non-invasively heat the stent and its surrounding plaque. Using Palmaz-Schatz stents as well as several stent-shape biopolymer materials embedded inside the phantom, Naguib, et al. continuously mapped rise in temperatures in the system upon ultrasound and microwave irradiations in separate settings. Temperature monitoring was done using a 12-channel ultra-thermometer (0.01° C.) with thermocouples (ultrasound) and fiber optic sensors (microwave). Therapeutic ultrasound at the frequency of 1-3 MHZ and intensity of 0.5-2.5 W/CM2 was used. Microwave radiofrequency was delivered by an antenna using a frequency of 2.45 GHZ and a power of 5.37 & 10.22 watts. In their ultrasound experiment Naguib, et al. found that the temperature of outer surface of stent and its surrounding tissue increased significantly higher than other sites. The rise in temperature varies by the type of biopolymer where silicon stent heated faster and more than polyurethane and polytetrafluoroethylene. Similar results were observed in the microwave experiments. Infrared thermography was used to measure the increased temperatures during delivery of both ultrasound and microwave radiation.

It is recognized, however, that externally applied forces, such as RF, microwave, ultrasound, etc. exist in the ambient environment. It is, therefore, undesirable to fabricate sensor device which will undergo a shape memory change upon encountering an ambient externally applied force. For example, it would be undesirable for a patient with an implanted sensor device responsive to microwave irradiation to have the implanted sensor device undergo a shape memory transition when the patient is warming food in a kitchen microwave appliance.

Because the microfabrication methods of the present invention allow for stringent control over the material composition of the implantable sensor device, the material composition may be made responsive to a particular frequency range that is outside the frequency range of the same type of energy signals existing in the ambient environment of the patient. Thus, both the device activation energy type and frequency and the detection energy type and frequency must fall outside that encountered in the ambient environment.

It is well known that metal stents are radioopaque and are detectable under radiographic imaging, such as fluoroscopy. Detection of the inventive sensor device may be accomplished by radiographic imaging, ultrasound imaging (either using frequencies which also generate a shape memory effect or not), magnetic resonance imaging, RF imaging or similar methods. The use of magnetic resonance imaging to image nitinol stents is known in the art. See, e.g., Randert, D, Hakim, B., Magnetic Resonance compatibility of Ni—Ti Stents, Abstract 8.P1, SMST-97 conference (International Organization on Shape Memory and Superelastic Technologies) found at URL http://www.fwsystems.com/professional/smstabs.html, in which they describe they studied the compatibility of Ni—Ti coronary stents using magnetic imaging to assess a) ferromagnetic forces; and b) artifacts. Two methods were used to measure force: horizontal sliding and pendulum deflection. Ferromagnetic forces were found to be less than 10% of stent weight. Artifacts were assessed to be small.

The use of particulate paramagnetic metal iron oxide as a contrast medium to image and model vascular profiles under magnetic resonance imaging (MM) has been demonstrated by Mitra Rajabi, et al. at the University of Texas-Houston, Houston, Tex., United States and the University of Texas-Medical Branch at Galveston, Galveston, Tex., United States. In an abstract published for presentation at the ACC 2001, the American College of Cardiology Scientific Session scheduled for Mar. 18-21, 2001, the abstract may be found at URL: http://www.hotplaque.com/ACC/ACC2001%20abstracts.htm#5), Raj abi, et al. describe a technique for imaging plaque inflammation. Super paramagnetic iron oxide (SPIO) particles are magnetic resonance (MR) imaging contrast media that have a central core of iron oxide generally coated by a polysaccharide layer. They shorten the relaxation time, predominantly the T2 relaxation time. Rajabi, et al. hypothesized that inflamed vulnerable arteriosclerotic plaques would preferentially take up these nano-particles by virtue of macrophage infiltration, leaking vasa vasorum and fissured thin caps. To test their hypothesis, they injected 1-3 mmol Fe/kg super paramagnetic iron oxide to six Apo E deficient and two C57b1 mice through the tail vein, after first obtaining baseline MR imaging. Post-contrast MR imaging were performed in day 5 with the same parameters (TR=2.5, TE=0.012, FOX=6 6, slice thickness=2.0 mm, flip angle (orient)=trans, and matrices=256×256). The aorta at the level of kidney was selected for comparison of the baseline and post-contrast images. Rajabi, et al. found decreased signal intensity in SPIO injected Apo E deficient mice and no decrease in signal intensity in SPIO injected C57b1 mice.

Thus, it is known in the art that thermal energy may be imparted to implanted medical devices fabricated of metal either by transcatheter approaches using direct application of heat, such as by a laser catheter, or may be induced by directing microwave or ultrasound energy toward the implanted device. Moreover, it is known implanted medical devices fabricated of shape memory alloys may be detected in vivo using radiography, ultrasonography, MRI, or RF imaging or combinations thereof.

In accordance with the present invention, any of the foregoing methods of applying energy to the inventive sensor device, either directly through transcatheter application or indirectly through inductive methods, as well as any of the foregoing methods for detecting the state of the inventive sensor device in vivo may be employed to effectuate change in the state of the implanted device. The energy stimulus may be an endogenous energy stimulus selected from the group consisting of fluid pressure, fluid shear forces, body temperature, cellular binding or molecular binding. Alternatively, the energy stimulus may be an exogenous energy stimulus such as externally applied temperature, pressure, microwave, ultrasound, RF, ultraviolet, infrared, magnetic resonance, x-rays, beta or gamma irradiation.

Turning now the accompanying Figures, and in particular FIGS. 1-4 there is illustrated first and second embodiments of implantable in vivo sensor in accordance with the present invention.

Temperature Sensor

The inventive in vivo temperature sensor 10 consists generally of an implantable tubular member 12 having a central lumen 14, an abluminal wall surface 16, a luminal wall surface 18 and at least one of a plurality of sensor regions 20 integral with at least one of the abluminal wall surface 16 and the luminal wall surface 18 of the implantable tubular member 12. The flow vector F of a fluid over the surface of the sensor region 20 is illustrated in FIG. 3. Each of the at least one of a plurality of sensor regions further comprise a plurality of cantilever members 22 patterned in an array on the implantable tubular member 12. The implantable tubular member 12, the sensor 20 and the plurality of cantilever members may be fabricated of like materials, such as shape memory materials, or may be fabricated of different materials, e.g., the implantable tubular member 12 being fabricated of stainless steel and the sensor 20 and cantilever members 22 being fabricated of a shape memory material, such as nickel-titanium alloys. In accordance with the best mode contemplated for the present invention, the tubular member 12, the sensor 20 and the cantilever members will be fabricated of shape memory materials, such as nickel-titanium alloys. Where each of the plurality of cantilever members 22 are fabricated of a shape memory material, either individual cantilever members 22 or groups of cantilever members 22 within a single sensor 20 may be fabricated to have different martensite transition temperatures. Thus, for example, cantilever members 22a within sensor 20 may be fabricated to have a transition temperature of X degrees Centigrade, while cantilever members 22b are fabricated to have a transition temperature of X+1 degrees Centigrade, cantilever members 22c are fabricated to have a transition temperature of X+2 degrees Centigrade, etc. Alternatively all of the cantilever members 22 in a sensor 20 may have the same transition temperature, and a plurality of sensors 20 are provided such that sensor 20a has cantilever members having a transition temperature of X degrees Centigrade, while the plurality of cantilever members 22 in sensor 20b are fabricated to have a transition temperature of X+1 degrees Centigrade, and the plurality of cantilever members 22 in sensor 20c are fabricated to have a transition temperature of X+2 degrees Centigrade, etc.

Each of the plurality of cantilever members 22 may be fabricated of a material capable of undergoing elastic, plastic, shape memory and/or a superelastic deformation. Materials such as stainless steel, titanium, nickel, tantalum, gold, vanadium, nickel-titanium, or alloys thereof may be employed to fabricate the plurality of cantilever members. Different electrical, thermal or mechanical properties may be imparted to the cantilever members 22 by altering the alloy ratios of the material. It is preferable to vacuum deposit both the tubular member 12, the sensors 20 and the cantilever members 22 to permit tight control over the material composition, electrical, mechanical and thermal properties of the material, as well as provide for tight control over the tissue and fluid contacting surfaces and the bulk material of the device. For example with nickel-titanium alloys, the titanium content of the target, in a nickel-titanium binary target, may be changed a known amount to precisely alter the transition temperature of a cantilever members.

Each of the plurality of cantilever members 22 preferably have binary functionality to provide a first "off" position indicative of an austenite phase of the cantilever members 22 and a second "on" position indicative of a martensite phase of the cantilever members 22. The first "off" position may be configured such that it is in a raised position which projects outwardly relative to the sensor 20 and/or the tubular member or in the lowered position that is substantially co-planar with the sensor 20 and/or the tubular member 12. Similarly, the second "on" position may be configured such that it is in a lowered position that is substantially coplanar with the sensor 20 and/or the tubular member 12 or the cantilever members 22 may be in the raised position or projecting outwardly relative to the sensor 20 and the tubular member 12, provided, however, that the first "on" position and the second "off" positions are different from one and other.

It will be understood, therefore, that as the implanted temperature sensor encounters different in vivo temperatures, different sets of cantilever members will be exposed to their transition temperature and change from the "off" position to the "on" position. In order to detect which cantilever members are in the "on" position and, therefore, determine the in vivo thermal conditions, the temperature sensor may be imaged radiographically, ultrasonically, magnetically or may be exposed to an external energy source which returns a signal representative of the number and position of the cantilever members that are in the "on" position. The returned signal may be generated by a passive transmitter embedded in solid state circuitry defined within the sensor 20, wherein the cantilever members 20 serve as electromechanical switches which alter a property of the solid state circuitry, for example, impedance or capacitance, and which then returns a detectable signal representative of the number and position of cantilever members 22 in the "on" position.

Pressure Sensor

Because it is structurally virtually identical to the temperature sensor 10, described above, the inventive in vivo pressure sensor will also be described with reference to FIGS. 1-4 and use identical reference numerals to describe the elements thereof. The inventive in vivo pressure sensor 10 consists generally of an implantable tubular member 12 having a central lumen 14, an abluminal wall surface 16, a luminal wall surface 18 and at least one of a plurality of sensor regions 20 integral with at least one of the abluminal wall surface 16 and the luminal wall surface 18 of the implantable tubular member 12. Each of the at least one of a plurality of sensor regions further comprise a plurality of cantilever members 22 patterned in an array on the implantable tubular member 12. The implantable tubular member 12, the sensor 20 and the plurality of cantilever members may be fabricated of like materials, such as superelastic materials, or may be fabricated of different materials, e.g., the implantable tubular member 12 being fabricated of stainless steel and the sensor 20 and cantilever members 22 being fabricated of a superelastic material, such as nickel-titanium alloys. In accordance with the best mode contemplated for the present invention, the tubular member 12, the sensor 20 and the cantilever members will be fabricated of superelastic materials, such as nickel-titanium alloys. Where each of the plurality of cantilever members 22 are fabricated of a superelastic material, either individual cantilever members 22 or groups of cantilever members 22 within a single sensor 20 may be fabricated to have different martensite transition temperatures. Thus, for example, cantilever members 22a within sensor 20 may be fabricated to have a martensitic stress/strain transition coefficient σ, while cantilever members 22b are fabricated to have a transition coefficient σ+1, cantilever members 22c are fabricated to have a transition coefficient of σ+2, etc. such that different cantilever members 22 or groups of cantilever members 22 change their position based upon a given quantum of stress or strain applied to the cantilever members 22 in vivo. Alternatively all of the cantilever members 22 in a sensor 20 may have the same transition temperature, and a plurality of sensors 20 are provided such that sensor 20a has cantilever members having a transition coefficient σ, while the plurality of cantilever members 22 in sensor 20b are fabricated to have a transition coefficient of σ+1, and the plurality of cantilever members 22 in sensor 20c are fabricated to have a transition coefficient of σ+2, etc. such that different sensors 20a, 20b, 20c respond to different stress-strain conditions.

Each of the plurality of cantilever members 22 may be fabricated of a shape memory and/or a superelastic material. Different electrical, thermal or mechanical properties may be imparted to the cantilever members 22 by altering the alloy ratios of the material. It is preferable to vacuum deposit both the tubular member 12, the sensors 20 and the cantilever members 22 to permit tight control over the material composition, electrical, mechanical and thermal properties of the material, as well as provide for tight control over the tissue and fluid contacting surfaces and the bulk material of the device. For example with nickel-titanium alloys, the titanium content of the target, in a nickel-titanium binary target, may be changed a known amount to precisely alter the transition temperature of a cantilever members.

Each of the plurality of cantilever members 22 may have binary functionality to provide a first "off" position indicative of an austenite phase of the cantilever members 22 and a second "on" position indicative of a martensite phase of the cantilever members 22. The first "off" position may be configured such that it is in a raised position which projects outwardly relative to the sensor 20 and/or the tubular member or in the lowered position that is substantially co-planar with the sensor 20 and/or the tubular member 12. Similarly, the second "on" position may be configured such that it is in a lowered position that is substantially coplanar with the sensor 20 and/or the tubular member 12 or the cantilever members 22 may be in the raised position or projecting outwardly relative to the sensor 20 and the tubular member 12, provided, however, that the first "on" position and the second "off" positions are different from one and other.

Alternatively rather than having merely binary functionality, each of the plurality of cantilever members 22 may have a response curve which is dependent upon the modulus of the material and the moment of inertia of each cantilever member. Each of the cantilever members 22 may be configured to have a variation in Z-axis thickness along an X-Y axis of the cantilever member 22. By configuring the cantilever members 22 with variable Z-axis thicknesses, different cantilever members 22 or different groupings of cantilever members will exhibit different stress-strain responses due to the different material modulus and different moment of inertia attendant to the altered geometry of the cantilever member 22. With this alternate construct of the cantilever members 22, for a given quantum of stress-strain applied to the cantilever members 22, the cantilever members 22 will deflect and shift a returned resonance frequency applied from an external energy source. The degree of deflection will then correlate to the stress and strain forces acting upon the cantilever members 22. It will be understood, of course, that this alternate construct of the cantilever members 22 still provides binary "on" and "off" functionality with the "on" and "off" positions merely being indicative of the outlying positions of the cantilever member 22.

It will be understood, therefore, that as the implanted pressure sensor encounters different stress and strain associated with, for example, changes in physiological blood pressure, fluid shear stress, endothelialization, arterioschlerotic plaque development, different sets of cantilever members will be exposed to their transition conditions and change from the "off" position to the "on" position. In order to detect which cantilever members are in the "on" position and, therefore, determine the stress-strain conditions, the pressure sensor may be imaged radiographically, ultrasonically, magnetically or may be exposed to an external energy source which returns a signal representative of the number and position of the cantilever members that are in the "on" position. The returned signal may be generated by a passive transmitter embedded in solid state circuitry defined within the sensor 20, wherein the cantilever members 20 serve as electromechanical switches which alter a property of the solid state circuitry, for example, impedance or capacitance, and which then returns a detectable signal representative of the number and position of cantilever members 22 in the "on" position.

With both the temperature sensor and pressure sensor embodiments, the cantilever members 22 may also be insulated from either the implantable tubular member 12 or from the sensor region 20. Thermal or electrical insulators may be positioned intermediate the sensor region 20 and the implantable tubular member 12 to insulate the implantable tubular member 12 from heat or electrical transfer from the cantilever members 22 to the implantable tubular member 12.

Vascular Imaging Sensor

We turn now to FIGS. 5-7B, in which there is illustrated the inventive in vivo sensor device 30 in the form of an endoluminal stent adapted for non-invasive vascular modeling and imaging. The inventive in vivo sensor device 30 comprises a plurality of structural elements 32, 36 that serve to define walls of the sensor device 30. The particular geometry of the plurality of structural elements 32, 36 may be selected based upon the intended function of the sensor device 30, e.g., a stent or stent-graft, and is not a significant factor in the present invention. It will be appreciated by those of ordinary skill in the art that alternative geometries of the structural elements 32, 36 other than those depicted in the Figures are contemplated by the present invention. The plurality of structural elements 32, 36 which define the sensor device 30 are fabricated of at least one of a shape memory materials, superelastic materials, plastically deformable materials and/or elastically deformable materials, such as stainless steel and/or nickel-titanium alloys, that permit the sensor device 30 to expand within an anatomical passageway, for example a blood vessel, at body temperature, i.e., the martensite transition temperature (in the case of a shape memory material) is below, but in proximity to, body temperature. In order to provide sensor functionality and permit vascular imaging and modeling, the inventive sensor 30 further comprises regions of the structural elements 32, 36 which have a second shape memory and/or superelastic material therewith (hereinafter the "second material"), which has, for example, a martensite transition temperature (or σ coefficient) which is higher than that of the base material for the structural elements 32, 36. Having a second material with either a higher transition temperature or a higher σ coefficient, allows for changing device 30 geometry or conformation upon application of internally or externally applied forces. For example, heat energy may be applied by either external microwave transmissions directed from outside the body to the device 30 or by a laser catheter that is used to apply laser energy to the sensor device 30. In either case, localized heating of the sensor device 30 to above the transition temperature of the second material causes the structural elements 32, 36 to undergo martensitic transformation with a concomitant change to the geometry and/or conformation of the sensor device 30. Upon martensitic transformation, at least some of the structural elements 32, 36 will change their positioning relative to the geometry of the sensor 30, as represented by arrows 38 in FIG. 6, thereby changing the configuration of openings 37 between adjacent pairs of structural elements 32, 36. The sensor 30 in its changed geometry and/or conformation may then be imaged using conventional non-invasive imaging techniques to provide an image of the vascular profile.

After retrieving a diagnostic image of the vascular profile, it may be necessary to remodel either the geometry or conformation of the sensor device 30. For example, the device 30 may require elongation or diametric enlargement (as depicted in FIGS. 7A and 7B). In order to remodel the sensor device 30, a superelastic material may be included in some of the structural elements 32, 36 which is responsive to externally applied forces, e.g., ultrasound, irradiation, microwave, ultrasound, RF, ultraviolet, infrared, magnetic resonance, x-rays and gamma irradiation, which will alter the stress-strain applied to the sensor device 30, causing a martensitic transformation in those portions of the structural elements 32, 36 and a concomitant change in the conformation of device 30.

Additionally, because thermal changes in the sensor device 30 may be induced by externally applied force, it is possible to both thermally heat, and thermally cool the sensor device 30. Ex vivo cooling may be accomplished by dampening the molecular vibrations induced by an external energy source, such as by shifting the frequency of the excitatory signal by 180 degrees. By dampening the molecular vibrations, a cooling effect may be generated in the sensor device 30 in order to induce localized cooling in the region of the sensor device 30.

Endoluminal Sensor

Also with reference to FIGS. 4-7B there is illustrated a sensor device 30 which comprises a generally tubular member having a plurality of wall elements 32, 36 that define walls of the sensor device 30. The plurality of wall elements are preferably fabricated of shape memory or superelastic materials such that the endoluminal sensor device 30 effectively has at least two martensite transition points. Conventional shape memory and superelastic materials have a single martensite transition point. However, by fabricating all of the wall elements 32, 36 of laminates of shape memory or superelastic materials such that one ply has a martensite transition point of $T_1$ and a second ply has a martensite transition point of $T_2$ wherein $T_2 > T_1$, the first ply will cause the sensor device 30 to transition at $T_1$ which corresponds to the condition for normal in vivo physiological conditions, while the an additional quantum of energy, such as externally applied microwave, ultrasound, RF energy or internally applied energy, such as laser irradiation or direct thermal contact, will induce the condition suitable for transition at $T_2$ and the device will undergo a second shape transition. Alternatively, portions of the wall elements 32, 36 may be fabricated of a first material having a transition point $T_1$, while other portions of the wall elements 32, 36, which are preferably non-structural for the sensor device 30 under the $T_1$ conditions, but are structural for the sensor device 30 under $T_2$ conditions, are fabricated of a second material having a transition point $T_2$. Thus, those wall elements 32, 36 fabricate of the $T_1$ material will cause the sensor device 30 to transition into an initial endoluminal shape or geometry under the conditions appropriate to achieve transition point $T_1$, while those wall elements 32, 36 fabricated of the $T_2$ material will not transition until the appropriate conditions for transition point $T_2$ are applied to the sensor device 30.

Endothelialization BioSensor

Turning now to FIGS. 8-10 there is illustrated a biosensor 40 for sensing endothelialization events at the tissue-contacting surface of the sensor device. Like the inventive in vivo sensor devices described above, the inventive biosensor 40 consists generally of an implantable substrate carrier 42 having tissue contacting surfaces 42, 46 thereupon. For purposes of illustration only, biosensor 40 is depicted with the implantable substrate carrier 42 being of a generally tubular configuration, such as for example, as stent. A plurality of binding regions 50 are defined on either of the tissue contacting surfaces 42, 46. The binding regions 50 are similar to the sensor regions of the above-described embodiments, except the binding regions 50 comprise regions of the implantable substrate carrier 42 which have biochemical markers, such as antibodies or ligands, bound thereto which are specific for endothelial and/or smooth muscle cell surface proteins or precursors of endothelial cell and smooth muscle cell proliferation, such as vascular endothelial growth factor or other growth factors. The material of the implantable substrate carrier 42 is preferably fabricated of a shape memory or superelastic material, which, upon binding of biological material to the biochemical markers in the binding regions 50, undergoes phase transformation due either the binding to the biochemical markers alone or in combination with an applied energy to the bound complex. The phase transformation of the material of the implantable substrate carrier 42 will cause a frequency shift in a returned signal from the applied energy source and will be indicative of the bound state of the binding domains 50.

With particular reference to co-pending, commonly assigned U.S. Patent Application Ser. No. 60/064,916, filed Nov. 7, 1997 which was published as PCT International Application WO9923977A1 entitled Intravascular Stent And Method For Manufacturing An Intravascular Stent, both of which are hereby incorporated by reference, the binding regions 50 may also form putative microgrooves 50 which are regions of the implantable substrate carrier 42 having patterned weakened atomic bonds in the crystalline structure of the substrate carrier 42 material. Upon binding of an endothelial cell, smooth muscle cell or a precursor thereof to the binding domain, the material of the substrate carrier 42 may either directly undergo or be induced by an external energy source to undergo a phase transformation which will cause the weakened atomic lattice of the crystalline structure of the substrate carrier 42 material to fracture and open a plurality of microgrooves 52 contiguous with the at the binding regions 50. The microgrooves 52 may be propagated by the additional binding of biological material to the markers at the binding regions 50. In this manner, there are self-propagating microgrooves which facilitate endothelialization of the implanted substrate carrier.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A method of using a sensor device, the method comprising the steps of:

inserting the sensor device into a lumen, wherein the sensor device comprises a plurality of sensor structural elements and a plurality of device structural elements, the plurality of sensor structural elements being formed as at least one vacuum deposited layer extending from or integral to at least some of the plurality of device structural elements, at least some of the plurality of sensor structural elements having either a first region with a first region geometry or first region conformation, the first region being composed of a first material, the first material having a first transition temperature and a first transition coefficient, or at least some of the plurality of sensor structural elements having a second region with a second region geometry or second region conformation, the second region being composed of a second material wherein the second material comprises at least one of a shape memory material and a superelastic material, the second material having a second transition temperature higher than the first transition temperature or a second transition coefficient higher than the first transition coefficient;

applying an internal or external thermal force to the sensor device;

increasing the temperature of the second material with the internal or external thermal force to exceed the second transition temperature;

changing the second region geometry or second region conformation and further changing the positioning of the second region relative to the first region geometry or first region conformation; and detecting a change in the second region geometry or second region conformation with a detection mechanism.

2. The method as defined in claim 1, further comprising a step of remodeling the sensor device after the step of changing the second region geometry or second region conformation and further changing the positioning of the second region relative to the first region geometry or first region conformation or after the step of detecting a change in the second region geometry or second region conformation with a detection mechanism, wherein the step of remodeling the sensor device comprises re-applying the external thermal force or internal thermal force or applying a second external thermal force or a second internal thermal force to the sensor device to make additional changes to the second region geometry or second region conformation.

3. The method as defined in claim 2, wherein the step of remodeling the sensor device further comprises altering stress or strain applied to the sensor device through the application of the external thermal force or internal thermal force or the second external thermal force or the second internal thermal force.

4. The method as defined in claim 2, wherein the step of remodeling the sensor device comprises selecting and applying the second external thermal force wherein the second external thermal force is selected from the following: ultrasound, irradiation, microwave, ultrasound, RF, ultraviolet, infrared, magnetic resonance, x-ray irradiation and gamma irradiation and applying the selected second external force to the sensor device.

5. The method as defined in claim 1, wherein the step of applying the internal or external thermal force further comprises selecting and applying an external thermal force and the external thermal force causes an excitatory signal that induces molecular vibrations of the sensor device and wherein the step further comprises cooling of the sensor device through dampening the molecular vibrations of the sensor device.

6. The method as defined in claim 5, wherein dampening the molecular vibrations of the sensor device comprises shifting a frequency of the excitatory signal of the external thermal force by 180 degrees.

7. The method as defined in claim 1, wherein the first material comprises a shape memory material.

* * * * *